(12) United States Patent
Suzuki et al.

(10) Patent No.: US 9,390,823 B2
(45) Date of Patent: Jul. 12, 2016

(54) RADIATION IMAGE ACQUIRING DEVICE

(71) Applicant: HITACHI, LTD., Tokyo (JP)

(72) Inventors: Atsuro Suzuki, Tokyo (JP); Takafumi Ishitsu, Tokyo (JP); Isao Takahashi, Tokyo (JP); Wataru Takeuchi, Tokyo (JP); Keiji Kobashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/433,387

(22) PCT Filed: Oct. 3, 2013

(86) PCT No.: PCT/JP2013/076988
§ 371 (c)(1),
(2) Date: Apr. 3, 2015

(87) PCT Pub. No.: WO2014/054755
PCT Pub. Date: Apr. 10, 2014

(65) Prior Publication Data
US 2015/0262721 A1    Sep. 17, 2015

(30) Foreign Application Priority Data

Oct. 4, 2012   (JP) .................... 2012-222548

(51) Int. Cl.
*G01N 23/04* (2006.01)
*G21K 1/02* (2006.01)
(Continued)

(52) U.S. Cl.
CPC ............... *G21K 1/02* (2013.01); *G01N 23/046* (2013.01); *G01T 1/1648* (2013.01); *G21K 1/04* (2013.01)

(58) Field of Classification Search
CPC .......... G01T 1/167; G01T 7/00; G01N 23/06; G01N 23/04; A61B 6/583; A61B 6/032; A61B 6/482; A61B 6/484; A61B 6/504; A61N 5/1048

See application file for complete search history.

(56) References Cited

U.S. PATENT DOCUMENTS

2012/0232385 A1*  9/2012  Hattori .................. G01T 1/1648
                                                            600/436

FOREIGN PATENT DOCUMENTS

JP          2001-343462 A     12/2001
JP             3928647 B2      3/2007
(Continued)

OTHER PUBLICATIONS

Translated document JP 5249694 is the machine translation of JP 2010078350. JP 5249694 is the published version of JP 2010078350.*

(Continued)

*Primary Examiner* — David Porta
*Assistant Examiner* — Mamadou Faye
(74) *Attorney, Agent, or Firm* — Mattingly & Malur, PC

(57) ABSTRACT

There is provided is a radiation image acquiring device which corrects a positional displacement between a collimator and a detector and obtains an image without artifacts. The device includes a detector (21) to measure a radiation; a collimator (26) including a through-hole (27) having one or more detectors (21) disposed therein and configured to limit an incident direction of the radiation; a positional displacement measuring unit configured to measure a positional displacement between the detector (21) and the collimator (26) by use of a profile of a radiation source measured by the detector (21) based on the radiation source disposed corresponding to a predetermined detector (21).

18 Claims, 14 Drawing Sheets

(51) Int. Cl.
*G01T 1/164* (2006.01)
*G21K 1/04* (2006.01)

(56) References Cited

FOREIGN PATENT DOCUMENTS

| JP | 2010-78350 A | | 4/2010 |
|----|----|----|----|
| JP | 2010078350 | * | 4/2010 |
| JP | 2011-106887 A | | 6/2011 |
| JP | 2011-158259 A | | 8/2011 |
| WO | 2008/046971 A1 | | 4/2008 |

OTHER PUBLICATIONS

C. Robert et al., Simulation-based and experimental evaluation of HiSens, a new CdZnTe gamma-camera architecture; 2008 IEEE Nuclear Science Symposium Conference Record, pp. 4246-4251.

* cited by examiner

POSITIONAL DISPLACEMENT
AMOUNT =0%

POSITIONAL DISPLACEMENT
AMOUNT =7.14%

POSITIONAL DISPLACEMENT
AMOUNT =14.28%

RADIATION IMAGE ACQUIRING DEVICE

TECHNICAL FIELD

The present invention relates to a radiation image acquiring device having a pixelated measurement system to acquire an image of a distribution of incident radiation.

BACKGROUND ART

As application of a radiation measurement device to a device in the nuclear medicine field, there is a single photon emission computed tomography (SPECT) using a gamma camera. The SPECT provides a transaxial image by measuring a distribution of a compound containing a radioactive isotope. The mainstream of the conventional SPECT device is a combination of a scintillator made of a single crystal with multiple photomultiplier tubes. Such SPECT devices obtain the location of radiation by centroid computation. However, in such a method, the finest possible resolution is about 10 mm, which is insufficient for the practical use in clinical activity. Therefore, there has been a demand for SPECT devices having higher resolution.

There has recently been developed a pixelated detector as a device having higher resolution. Examples of the pixelated detector include one formed of a scintillator, one formed of a semiconductor, and the like. Any of such pixelated detectors acquire a position signal per unit of a small detector, i.e., per pixel. Therefore, the intrinsic special resolution of the detector is determined by the pixel size, and spatially discrete measurement is performed. There has been developed a device even having a pixel size of 1.2 mm, which achieves the resolution of 10 mm or less, resulting in significant improvement.

There has also been developed and improved a trans axial reconstruction method, making a significant contribution to the improvement in resolution. A filtered back-projection method (FBP method) and a successive approximation method (MLEM, OSEM or the like) without resolution recovery have heretofore been used. Furthermore, a successive approximation method with resolution recovery has also recently been developed. This method enables reconstruction considering geometric configurations of the collimator and the detector, and physical factors such as scattered radiation. Therefore, more accurate images is provided.

The following description of the pixelated detector is provided by using the terms "detector" and "detector group." The detector means one included in one pixel having any shape, while the detector group means an assembly of the detectors arrayed. The detector generally has a rectangular shape. When seen from the radiation incident side, the detector group has a configuration in which rectangles are densely packed. In order that all the detectors included in the detector group can have uniform sensitivity, the through-holes in the collimator and the detectors are often arranged on a one-to-one basis.

Moreover, in terms of ease in handling, the through-hole generally has a rectangular shape corresponding to the shape of the detector. When the detector has the rectangular shape, two to four surfaces of each detector come into contact with the adjacent detectors, and these surfaces are defined as "boundary surfaces of the detector". In the conventional device, the ceptor of the collimator is disposed on the boundary surface.

In this regard, there is a generally known problem that moire is generated when there is a positional displacement between the collimator and the detector. In order to solve this problem, there has been disclosed a configuration in which a collimator and a detector group are rotated relative to each other (Patent Literature 2). In this configuration, even when the collimator is displaced from a predetermined position, the area of the ceptor traversing the detector is maintained constant.

A SPECT imaging device with high spatial resolution and high sensitivity has been demanded in clinical practice. There are many factors that determine the resolution and sensitivity, such as a distance from a radiation source, the thickness of the ceptor, radiation energy, scatter, and absorption. Among these factors, the height of the ceptor and the size of the opening are significantly responsible for the determination of the resolution and sensitivity. In order to achieve high resolution, the arrival direction of radiation entering the detector needs to be limited by the collimator. Therefore, a field of view of the detector on the measurement target may be narrowed by the collimator. As such a collimator, there has been known a LEHR (low energy high resolution) collimator, for example. However, such limitation costs the sensitivity.

In order to achieve high sensitivity, the hole length of the collimator needs to be reduced. As such a collimator, there have been known a LEGP (low energy general purpose) collimator and a LEHS (low energy high sensitivity) collimator. However, the shortened hole length of the collimator deteriorates the resolution.

As described above, the conventional device cannot achieve both the high resolution and high sensitivity. Therefore, the collimators need to be replaced according to the purpose, leading to increased workload at a clinical site.

Therefore, as a device that achieves both sensitivity and resolution, a new type of SPECT device has been invented, including two or more detectors in one rectangular through-hole. This SPECT device has been proven to achieve higher resolution than the conventional device in which the through-holes and the detectors correspond on a one-to-one basis, when the SPECT and conventional devices have the through-holes in the same size (Patent Literature 1 and Non-Patent Literature 1).

CITATION LIST

Patent Literature

Patent Literature 1: PCT/FR2006/002360 (WO2008/046971) "Gamma-camera using the depth of interaction in a detector"
Patent Literature 2: Japanese Patent No. 3928647
Patent Literature 3: Japanese Patent Application Publication No. 2010-78350

Non-Patent Literature

Non-Patent literature 1: C. Robert et al. (2008) 2008 IEEE Nuclear Science Symposium Conference Record Vol. 6, pp. 4246-4251

SUMMARY OF INVENTION

Technical Problem

In the SPECT device, in order to acquire a uniform image without uneven sensitivity or artifacts, it is important to properly align the collimator and the detector with each other. Particularly, the SPECT device having a configuration, in which two or more detectors are included in one through-hole and the sides of the detectors and the sides of the ceptors coincide with each other, requires higher accuracy in alignment of the collimator than the conventional device in which the through-holes and the detectors correspond on a one-to-one basis. This is because of the following reasons.

In the configuration in which two or more detectors are included in one through-hole and the ceptors are disposed on the extensions of the boundary surfaces of the detectors, a positional displacement of the collimator exerts a more serious influence. In this case, the positional displacement of the collimator causes a cyclic streaky pattern to appear. This is because the ceptors are disposed on some of the detectors and no ceptors are disposed on the other some of the detectors. Therefore, a displacement of the collimator causes uneven sensitivity in a cyclic streaky pattern.

Note that since the uneven sensitivity is determined based on the positional relationship between the ceptors and the detectors, the cycle is about several pixels. It is known that ring artifacts occur when reconstruction is performed using measurement data with such streaky uneven sensitivity. The uneven sensitivity in short cycles causes artifacts in short cycles, and the fine structures in the transaxial image are lost, leading to significant deterioration in image quality. Therefore, the configuration, in which two or more detectors are included in one through-hole and the ceptors are disposed on the extensions of the boundary surfaces of the detectors, requires more precise alignment of the collimator.

As an alignment method for the conventional collimator in which the through-holes and the detectors correspond on a one-to-one basis, there has been proposed a method using the fact that a profile based on a predetermined radiation source is symmetrical when there is no positional displacement of the collimator (Patent Literature 3).

However, in the configuration in which two or more detectors are included in one through-hole, a profile based on a predetermined radiation source is not symmetrical even when there is no positional displacement of the collimator. The method of Patent Literature 3 cannot be adopted.

Therefore, it is an object of the present invention to provide a radiation image acquiring device capable of acquiring an image without artifacts by correcting a positional displacement between a collimator and a detector.

Solution to Problem

A radiation image acquiring device including: a detector configured to measure a radiation; a collimator including a through-hole having one or more detectors disposed therein and configured to limit an incident direction of the radiation; and a positional displacement measuring unit configured to measure a positional displacement between the detector and the collimator by use of a profile of a radiation source measured by the detector based on the radiation source disposed corresponding to a predetermined detector.

Advantageous Effects of Invention

The present invention provides a radiation image acquiring device capable of acquiring an image without artifacts by correcting a positional displacement between a collimator and a detector.

DESCRIPTION OF EMBODIMENTS

With reference to the drawings, a radiation image acquiring device according to the present invention is described below.

First Embodiment

Description is provided for a configuration of a SPECT system and image reconstruction firstly, and then for an influence of occurrence of a positional displacement of a collimator. At the end, a method for obtaining positional information of the collimator is described.

Figure 1:
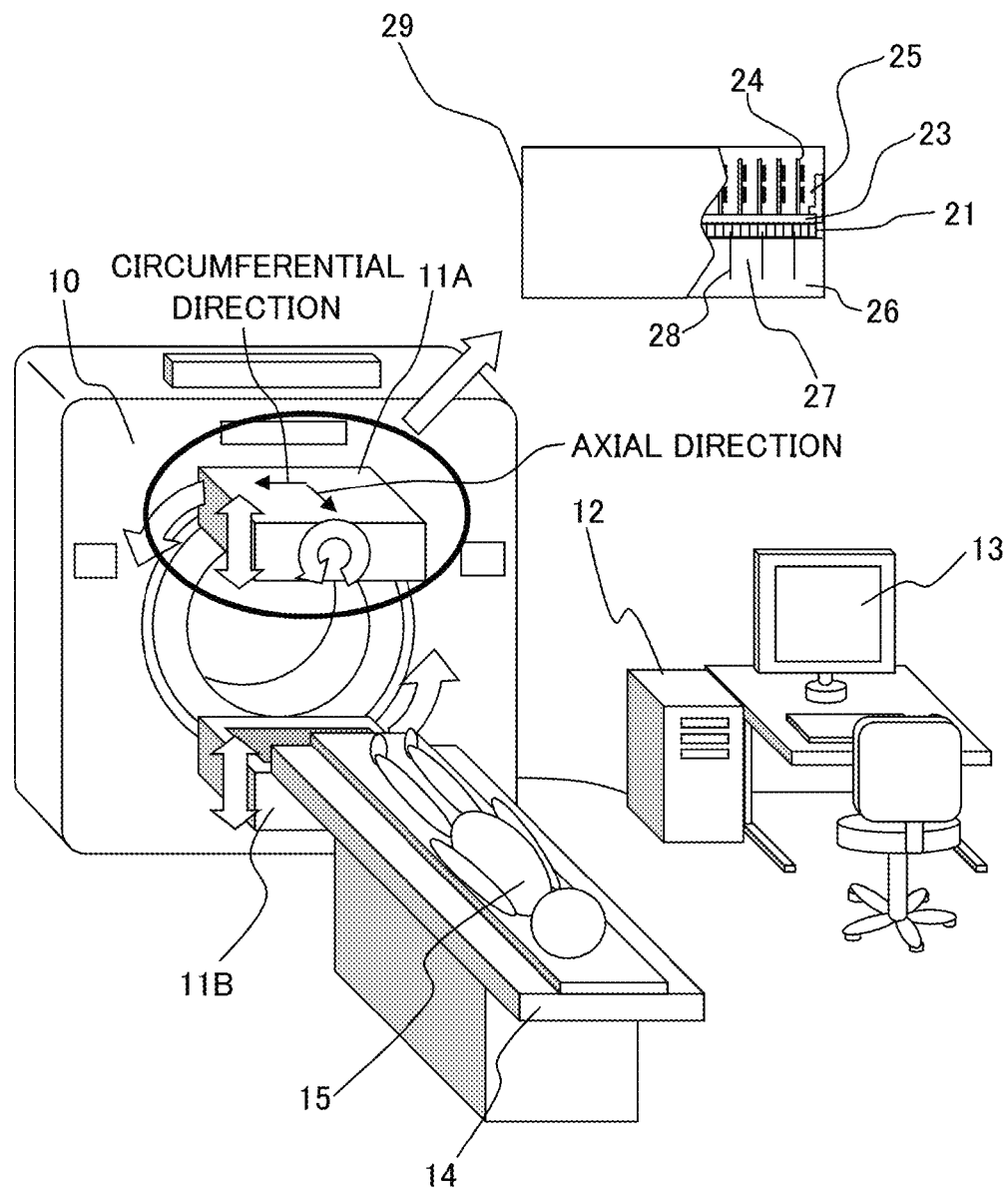
FIG. 1 is a diagram showing a SPECT system (gamma camera) using a radiation image acquiring device according to an embodiment of the present invention.

As shown in FIG. 1, the SPECT system includes a gantry 10, cameras (radiation image acquiring devices) 11A and 11B, a data processing device 12, a display device 13, and the like. A subject 15 receives a radioactive drug, e.g., a drug containing $^{99m}$Tc having a half-life of 6 hours. Emitted γ ray from $^{99m}$Tc in the body of the subject 15 lying down on a bed 14 are detected by the cameras 11A and 11B supported by the gantry 10 to acquire a transaxial image (tomographic image).

Since the cameras 11A and 11B have the same configuration, the camera 11A is described here. The camera 11A includes a collimator 26 and a detector 21. The collimator 26 has a function to screen the γ ray emitted from the body of the subject 15 and to allow only the γ ray in a certain direction to pass therethrough. The detector 21 detects the γ ray passing through the collimator 26. The camera 11A includes an application specific integrated circuit (ASIC) 25 for measuring a detection signal for γ ray (referred to as a γ ray detection signal).

As for the γ ray detection signal, an ID of the detector 21 that has detected the γ ray, a peak value of the detected γ ray, and detection time thereof are inputted to the ASIC 25 through a detector substrate 23 and an ASIC substrate 24. The detector 21, the detector substrate 23, the ASIC substrate 24, the ASIC 25 and the collimator 26 are surrounded by a light/γ ray/electromagnetic shield 29 made of iron, lead or the like to shield light, γ rays and electromagnetic waves. The data processing device 12 includes a storage unit and a transaxial image information creation unit (not shown). The data processing device 12 retrieves packet data including the detector (channel) ID and the data of the measured peak value and detection time of the γ ray to create a planar image or create transaxial image information by converting the packet data into sinogram data, and displays the created planar image or transaxial image information on the display device 13.

The cameras 11A and 11B is mobavable in a radial direction and a circumferential direction of the gantry 10. During shooting of a transaxial image, the cameras 11A and 11B are rotated about a gantry attachment part to identify the location of a tumor by detecting γ rays generated from the radioactive drug accumulated in the tumor or the like in the body of the subject 15.

Figure 5:
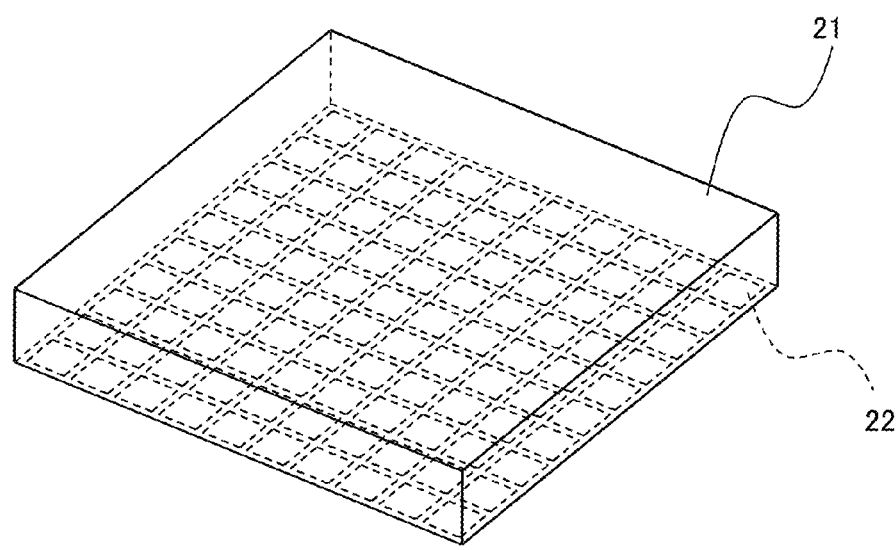
FIG. 5 is a diagram showing a second example of the pixelated detector.
Figure 6A:
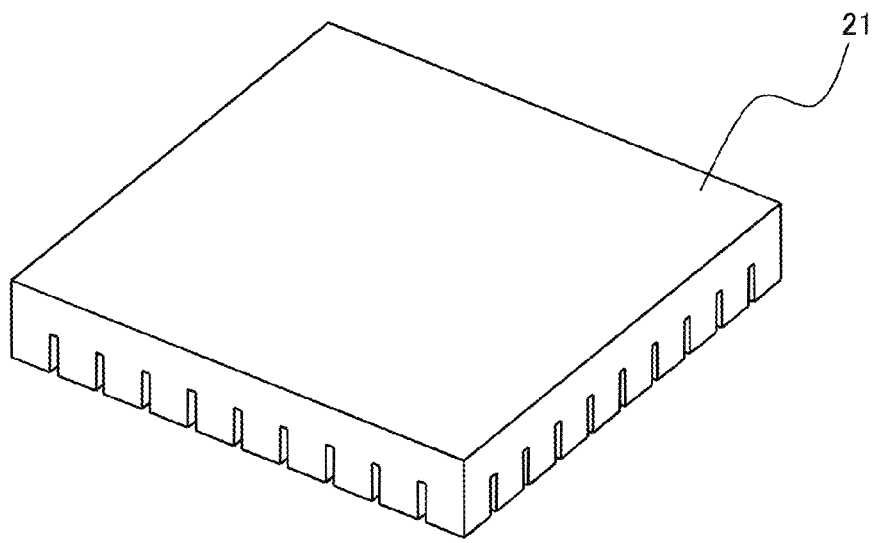
FIGS. 6A and 6B are diagrams showing a third example of the pixelated detector.
Figure 6B:
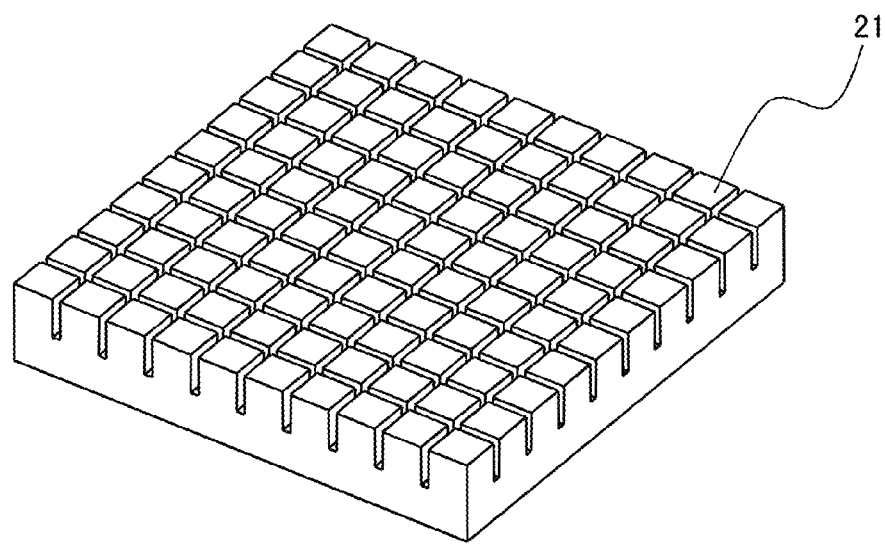
Figure 7:
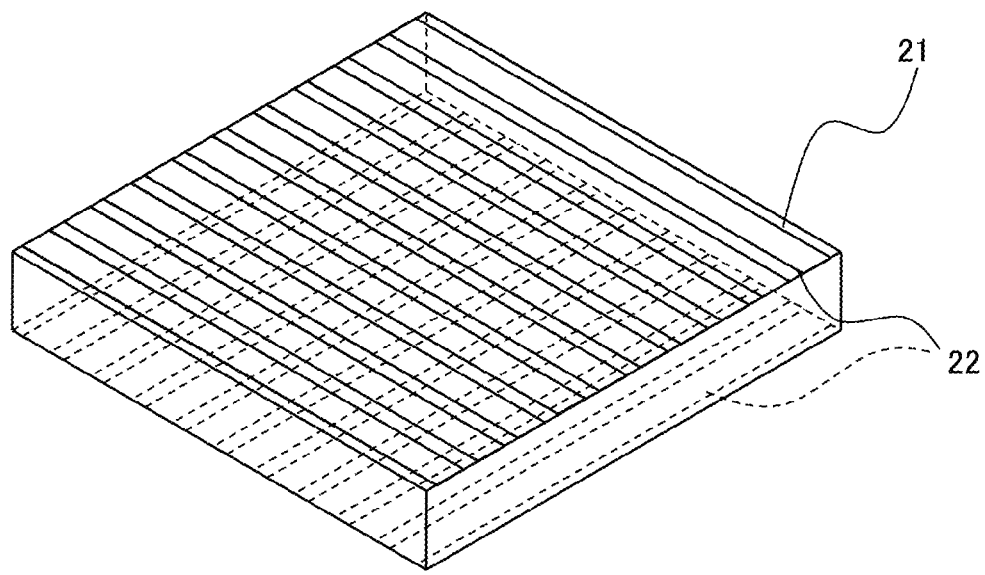
FIG. 7 is a diagram showing a fourth example of the pixelated detector.
Figure 8:
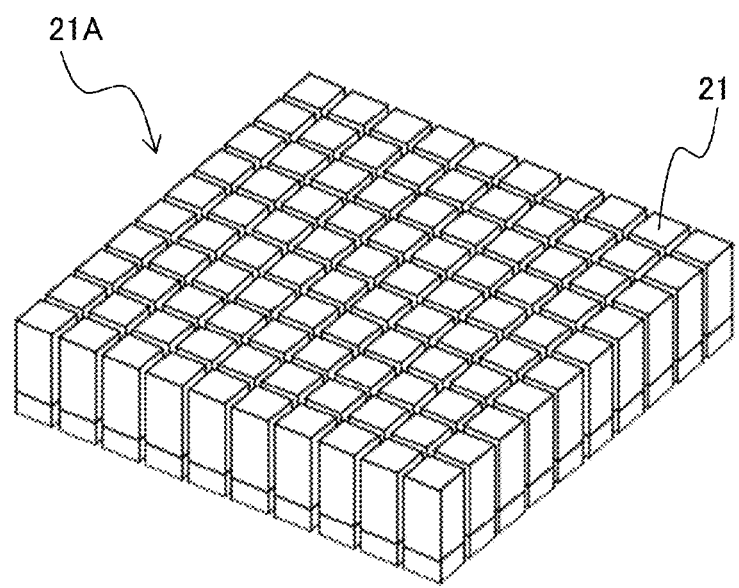
FIG. 8 is a diagram showing a fifth example of the pixelated detector.

As shown in FIGS. 4 to 8, the detector 21 is divided for each pixel, and a group of detectors 21A is configured, in which a number of the detectors 21 are arranged. Therefore, unlike a scintillator made of one large crystal, the detection signal is collected for each detector 21, i.e., for each pixel. Note that, although the group of detectors 21A is divided into pixels, an electrode 22 may be divided into pixels as shown in FIG. 5. Alternatively, as shown in FIGS. 6A and 6B, the detectors 21 may be partially integrally provided. As shown in FIG. 7, the electrodes 22 may be provided on the top and the bottom. As shown in FIG. 8, a scintillator and a panel detector may be combined.

Figure 3:
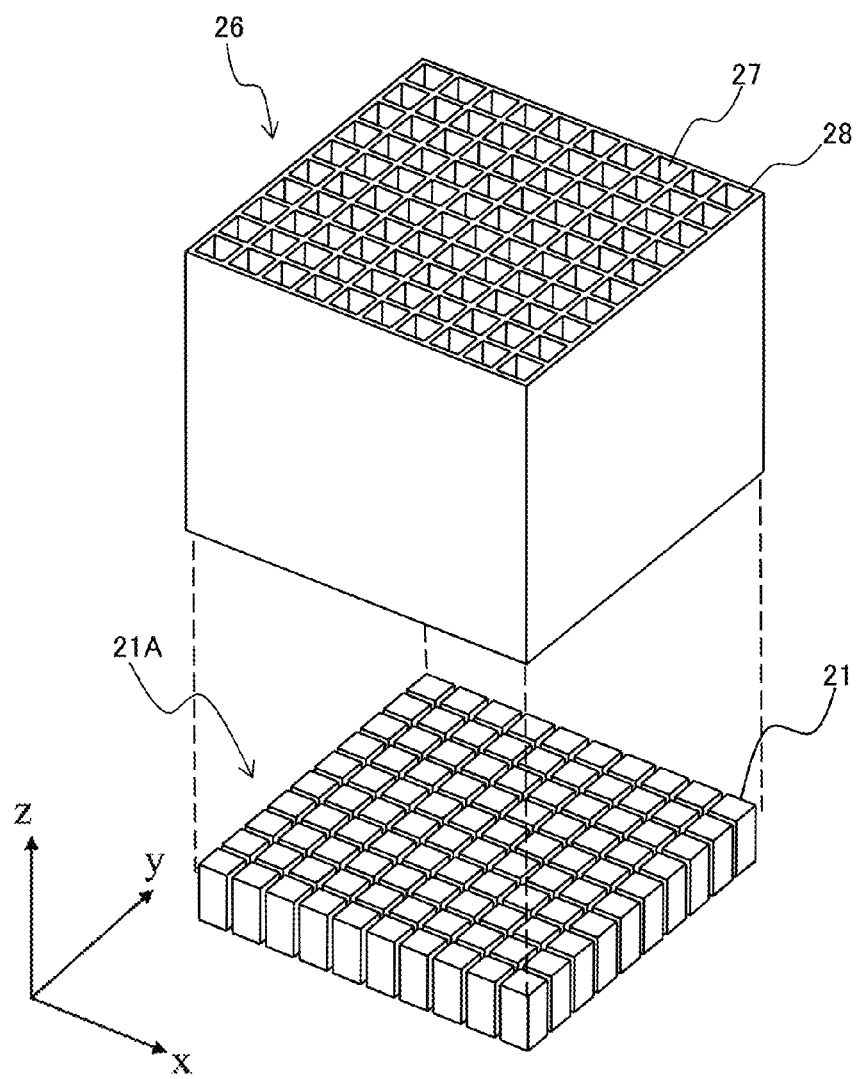
FIG. 3 is a diagram showing a general arrangement example of the pixelated detector and the collimator.
Figure 4:
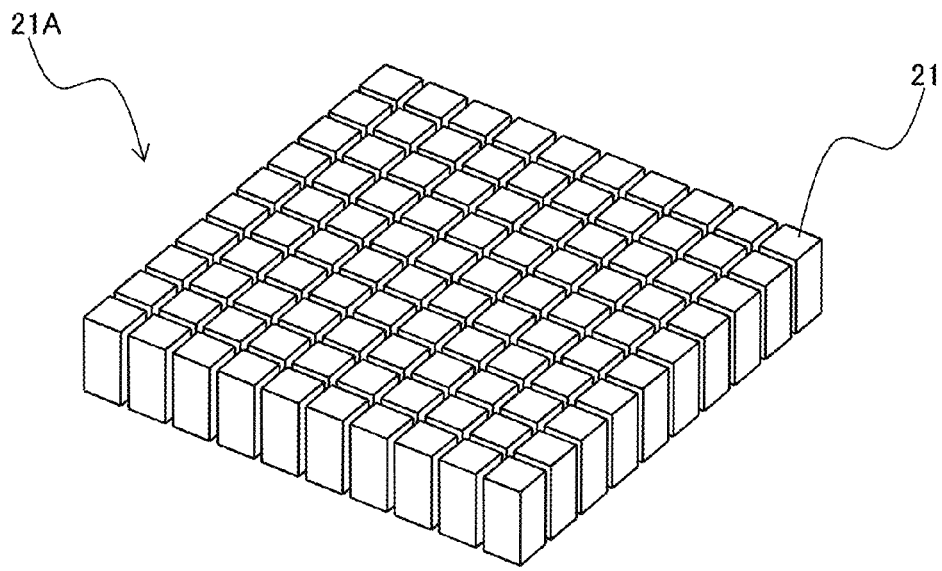
FIG. 4 is a diagram showing a first example of the pixelated detector.
Figure 9:
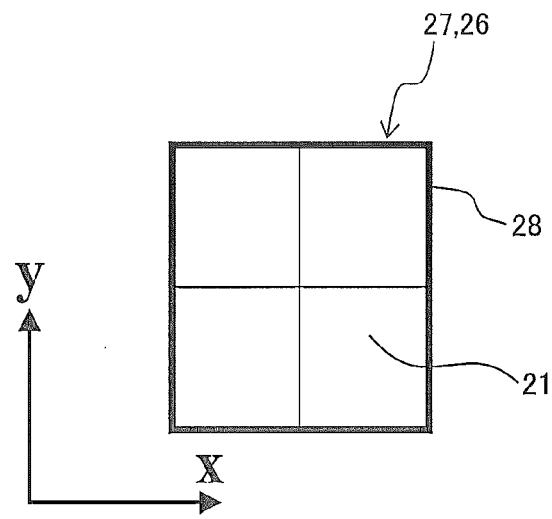
FIG. 9 is a diagram showing an arrangement example of a pixelated detector and a collimator.

As shown in FIG. 3, the collimator 26 made of lead has through-holes 27, and the through-holes 27 are arranged in a grid pattern. The through-holes 27 are compartmentalized by a ceptor 28. In general, the through-holes 27 and the detectors 21 correspond on a one-to-one basis. In this embodiment, description is given of the case where the area of an opening of one of the through-holes 27 in the collimator 26 is equal to the area of four detectors 21, as shown in FIG. 9.

However, the present invention is also applicable to the case where one through-hole 27 includes N (one or two or more) detectors. Note that, in the following description, it is assumed that x, y and z (shown only in FIG. 3) directions are specified and the detectors 21 are arranged within an xy plane, as shown in FIGS. 3, 9 and the like.

Next, description is given of image reconstruction executed by the data processing device. When the group of detectors 21A forms a certain angle with a measurement target, a count number $y_i$ of a certain detector i is obtained as follows: where $\lambda_j$ is a count number of detection reconstruction pixels j.

$$y_i = \Sigma C_{ij} \lambda_j \qquad \text{Expression (1)}$$

Here, $C_{ij}$ represents a probability of detection by the detector i. From Expression (1), an image is reconstructed using a successive approximation reconstruction method (MLEM, OSEM, MAP and the like). By incorporating a point response function of the detector 21 into successive approximation image reconstruction, spatial resolution is capable of being recovered. The point response function is a probability that the detector 21 detects radiation generated from a point radiation source, and is equal to the detection probability $C_{ij}$ in Expression (1). The use of the point response function enables a more accurate image to be reconstructed with the successive approximation reconstruction method such as MLEM and OSEM.

Figure 10:
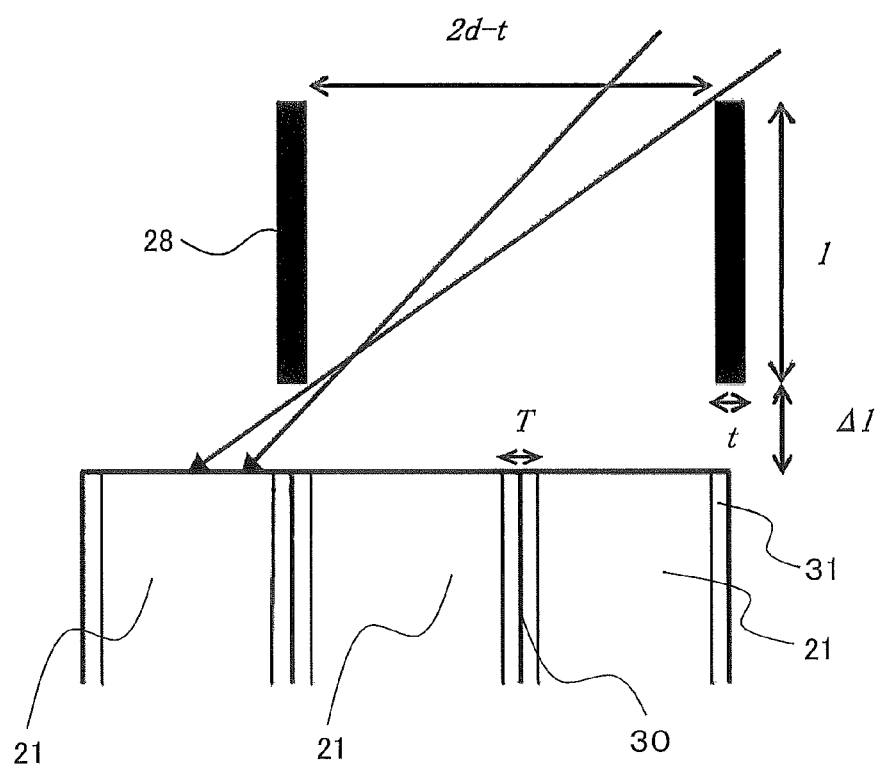
FIG. 10 is a diagram showing the cross-section of the pixelated detector and the collimator, and leakage radiation from the adjacent through-hole.

Next, with reference to FIG. 10, description is given of the influence by occurrence of a positional displacement of the collimator 26. As parameters shown in FIG. 10, l, Δl, t, d and T represent the height of the collimator 26, distance between the collimator 26 and the detector 21, thickness of the ceptor 28, length of one of the sides of the detector 21, and length of a dead region 31, respectively.

As shown in FIG. 10, it is difficult, due to the physical limitations, that the distance Δl between the detector 21 and the collimator 26 is set to 0. The leakage radiation from the adjacent pixel enters through a gap therebetween. The leakage radiation is detected by the detector 21 located near the ceptor 28. When the collimator 26 is displaced in the x direction, a distribution of the leakage radiation also changes along with the collimator 26. Therefore, when a positional displacement occurs between the collimator 26 and the detector 21, the count number of the radiation detected by the detector 21 changes, and the point response function also changes.

Figure 2:
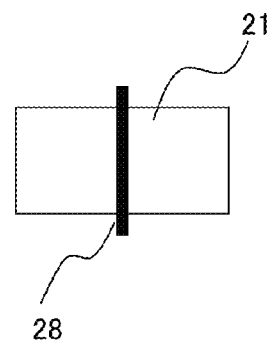
FIG. 2 is a diagram showing an arrangement example of a pixelated detector and a collimator (ceptor).
Figure 11A:
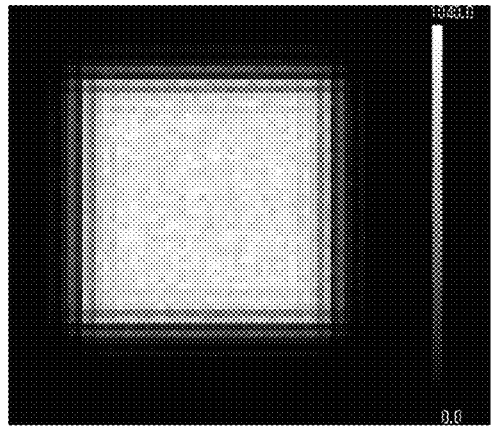
FIGS. 11A to 11C are diagrams showing results of imaging simulation when the detector and the collimator shown in FIG. 10 are used.
Figure 11B:
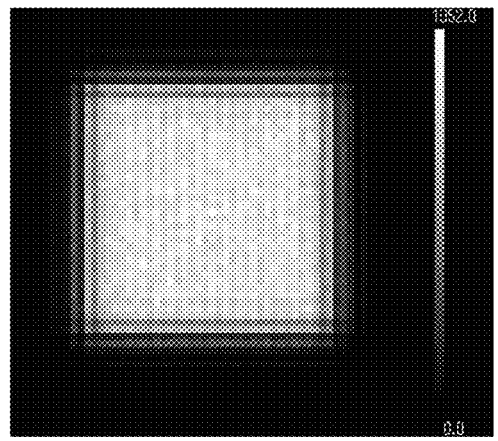
Figure 11C:
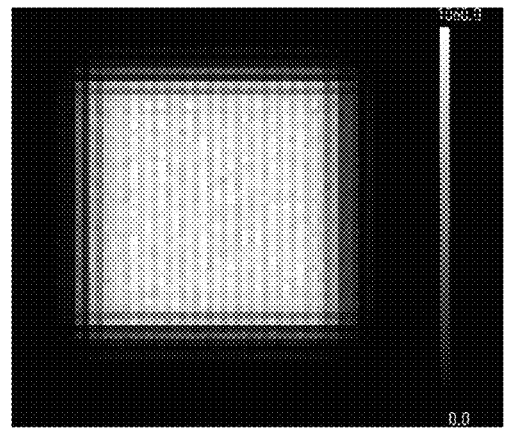

As shown in FIG. 2, the point response function when the detectors 21 are disposed with the ceptor 28 interposed therebetween changes significantly with respect to the displacement. When the number of the detectors included in the through-hole 27 is two or more, the ceptor 28 is located on a certain detector 21 if the collimator 26 is displaced. Thus, the absence of the ceptor 28 on the other detector 21 causes uneven sensitivity, leading to a change in the point response function. The uneven sensitivity appears as a cyclic streaky pattern. As an example, FIGS. 11A to 11C show simulated images obtained with the configuration shown in FIG. 9, in the case of irradiation of a uniform planar source. It is assumed that the planar source is placed in a position 50 mm above an upper end of the collimator 26, and that l=26 mm, Δl=6 mm, d=1.4 mm, and t=0.4 mm.

FIG. 11A shows the case where there is no displacement between the collimator 26 and the detector 21. FIG. 11B shows the case where the position of the collimator 26 is displaced by 7.14% (0.1 mm) of a detector pitch (1.4 mm) in the x direction from the no displacement state of FIG. 11A. Likewise, FIG. 11C shows the case where the position of the collimator 26 is displaced by 14.28% (0.2 mm).

When there is no positional displacement of the collimator 26, a uniform image is acquired. However, if even a slight positional displacement occurs, peaks and troughs corresponding to the count number appear alternately in lines perpendicular to the direction of the positional displacement.

Generally, when performing tomography, more than one planar image is acquired while changing the angle with respect to an object. It is known that, when a certain streaky pattern appears in the planar image regardless of the angle, a ring artifact appears in a reconstructed image. In the above case, since the uneven sensitivity is in short cycles, a short-cycle ring artifact occurs. The short-cycle artifact becomes a factor that destroys a fine structure of the transaxial image and significantly deteriorates image quality.

In this event, the ring artifact occurs even when reconstruction is performed with an image reconstruction method (FBP or the like) using no point response function. The cyclic pattern remains as the cyclic pattern even after the reconstruction, and becomes an artifact. The short-cycle artifact appears even in the case of successive approximation reconstruction using the point response function when there is "no displacement". This is because the point response function in the case where there is "no displacement" does not reproduce a cyclic pattern, recovery cannot be made.

Figure 12:
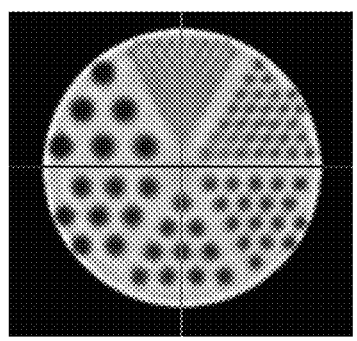
FIG. 12 is a diagram showing the result of image reconstruction simulation when the detector and the collimator shown in FIG. 10 are used.

FIG. 12 shows an image obtained by reconstructing projection data created by simulation from numerical phantom when there is no displacement of the collimator 26. In the numerical phantom, a region where a radioactive drug exists and a pixel value in a cold spot are set to 1 and 0, respectively.

Figure 13:
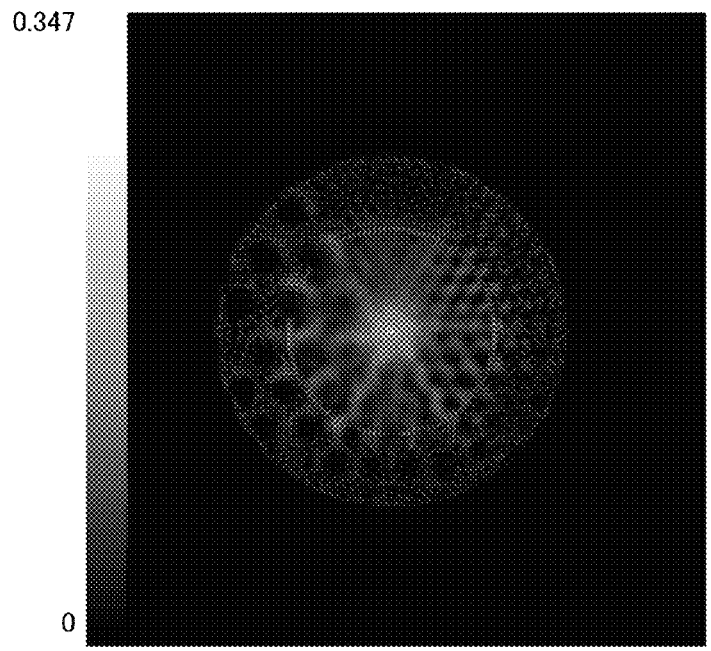
FIG. 13 shows an example of subtracting the result of FIG. 13 from the result of image reconstruction simulation when the collimator is displaced by 7% of a detector pitch from the state of the detector and the collimator shown in FIG. 10.

FIG. 13 shows an image of an absolute value of a difference between reconstructed images obtained by simulation when there is no displacement of the collimator 26 and when the position of the collimator 26 is displaced by 7% of the detector pitch in the x direction. It is confirmed that streaky artifacts appear. It is seen that these artifacts destroy the fine structure of the transaxial image and significantly deteriorate image quality.

Next, description is given of a method for obtaining an amount of positional displacement of the collimator 26.

Figure 14:
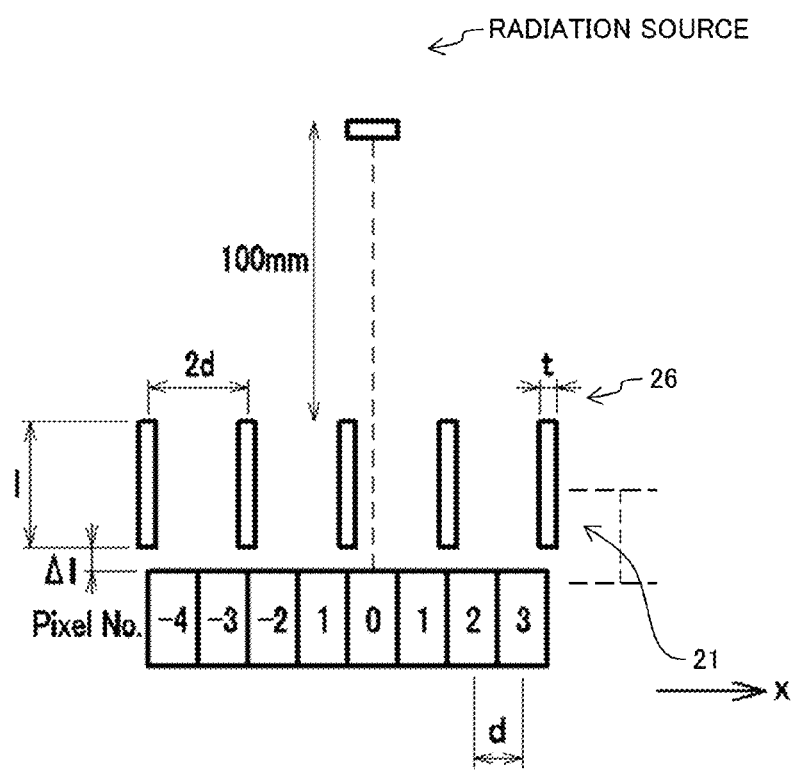
FIG. 14 is a diagram showing a positional relationship among a radiation source, the collimator and the detector during measurement of a positional displacement of the collimator.
Figure 15:
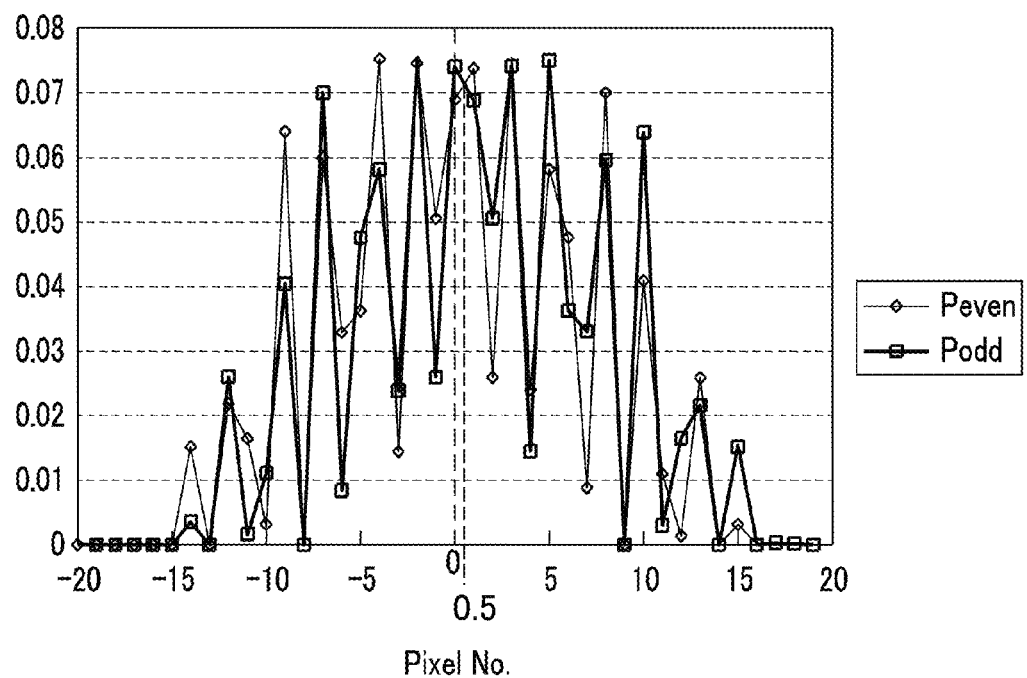
FIG. 15 is a diagram showing profiles $P_{even}$ and $P_{odd}$.

As shown in FIG. 14, considering the case where detectors are one-dimensionally arranged in the x direction, it is assumed that a profile measured when the radiation source is present on the even-numbered detector pixel (pixel No. 0) is $P_{even}$. Likewise, it is assumed that a profile measured when the radiation source is present on the odd-numbered detector pixel (pixel No. 1) (not shown) is $P_{odd}$. FIG. 15 shows $P_{even}$ and $P_{odd}$ obtained by ray trace simulation. Here, it is assumed that l=15 mm, Δl=13 mm, d=1.4 mm, and t=0.4 mm. It is also assumed that a distance between the radiation source and the upper end (surface) of the collimator 26 is 100 mm Meanwhile, FIG. 16 shows a profile $P_{odd'}$ (assuming the case where there is no positional displacement of the collimator 26) obtained by inverting $P_{odd}$ shown in FIG. 15 about pixel No. 0.5.

Figure 16:
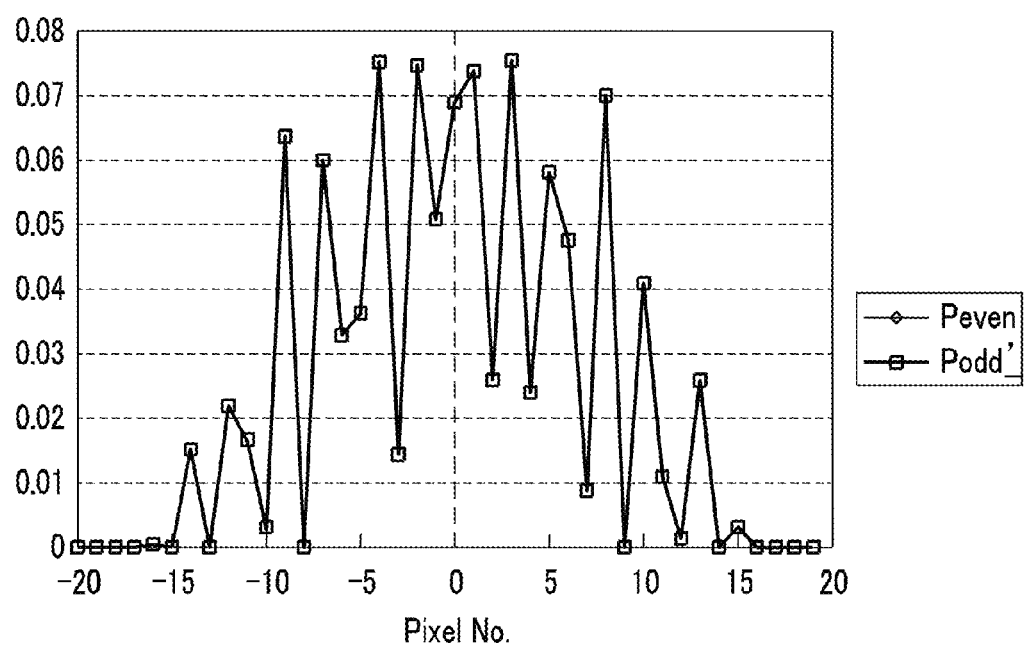
FIG. 16 is a diagram showing profiles $P_{even}$ and $P_{odd''}$.

As shown in FIG. 16, $P_{even}$ and $P_{odd'}$ coincide completely with each other. Therefore, when there is no positional displacement of the collimator, residual sum of squares of $P_{even}$ and $P_{odd'}$ is 0.

Figure 17:
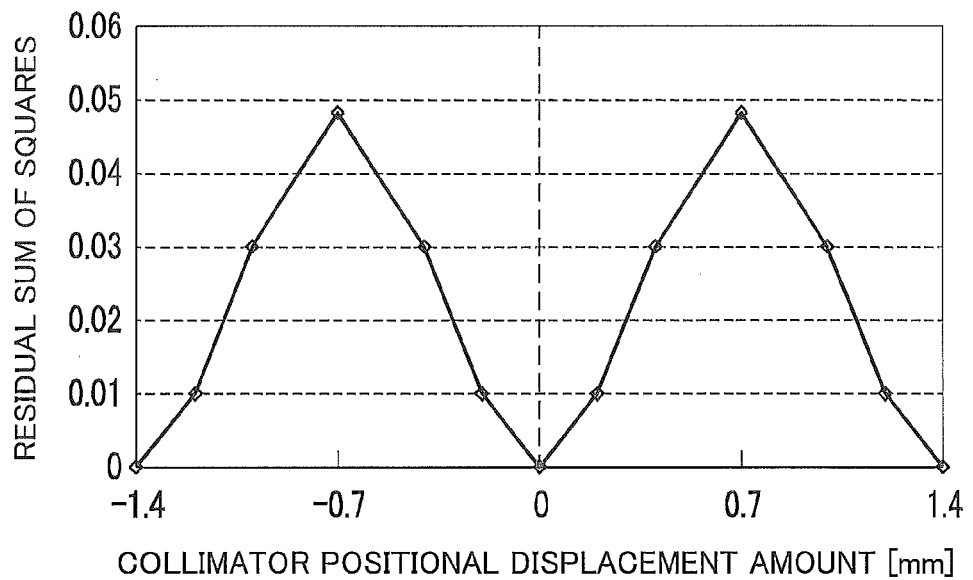
FIG. 17 is a diagram showing a relationship between a collimator positional displacement and the residual sum of squares of $P_{even}$ and $P_{odd''}$.

FIG. 17 shows a relationship between the amount of positional displacement of the collimator 26 in the x direction and the residual sum of squares of $P_{even}$ and $P_{odd'}$. As shown in FIG. 17, the residual sum of squares is increased when the positional displacement is increased in a positive direction. Due to the periodicity of the through-holes 27 in the collimator 26 and the detector pitch, the residual sum of squares reaches its peak when the positional displacement is 0.7 mm. A positional displacement in a negative direction also shows the same tendency.

As described above, by obtaining the residual sum of squares of $P_{even}$ and $P_{odd'}$ through measurement based on an arbitrary radiation source during alignment of the collimator 26, a positional displacement amount (a positional displacement amount $D_x$ in the x direction and a positional displacement amount $D_y$ in the y direction) is capable of being estimated from FIG. 17. Note that, as described above, $P_{even}$ and $P_{odd}$ may be obtained by disposing the radiation source on the even-numbered and odd-numbered detector pixels and measuring profiles.

Figure 18:
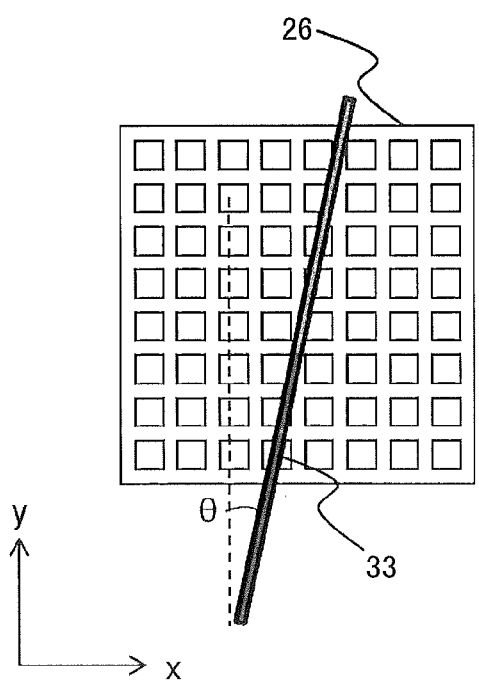
FIG. 18 is a diagram showing a state where a line source is disposed obliquely to the y-axis.

Alternatively, as shown in FIG. 18, $P_{even}$ and $P_{odd}$ may also be obtained in one measurement by disposing a line source 33 at an angle θ with respect to the y-axis (disposing the radiation sources such that the positions thereof are on the even-numbered or odd-numbered detector pixels) and measuring profiles in the x direction. In this event, it is required to determine whether or not the radiation source is located on the even-numbered or odd-numbered detector pixel. The positions of the radiation sources are capable of being determined by obtaining the positions of the centroids of the profiles obtained by the measurement, for example. The data processing device 12 includes a position identification unit for specifying such positions of the radiation sources.

Note that the profile in the y direction may be measured by disposing the line source 33 at the angle θ with respect to the x-axis (disposing the radiation sources such that the positions thereof are on the even-numbered or odd-numbered detector pixels).

Alternatively, if an X-ray CT device (originally equipped with an X-ray source) is available, the position may be determined from a CT image of the source. From a practical perspective, the measurement is performed using the line source 22 as shown in FIG. 18 to obtain the profile in the x direction for each of the detector pixel positions in the y direction, and thus obtain the position of the centroid of each profile in the x direction. Note that the use of the X-ray source of the X-ray CT device eliminates the need to separately prepare the line source 33.

Here, the profile in the x direction is expressed by the count in the vertical axis while designating the detector pixel positions with integers in the horizontal axis. Then, after sorting out the rounded values of the positions of the centroid between even numbers and odd numbers, average values of profile groups corresponding to the sorted even numbered and odd numbered pixels may be set as $P_{even}$ and $P_{odd}$, respectively.

Such acquisition of the amount of positional displacement of the collimator 26 is performed by the data processing device 12.

Next, description is given of a method for determining a positional displacement direction of the collimator 26.

Figure 19:
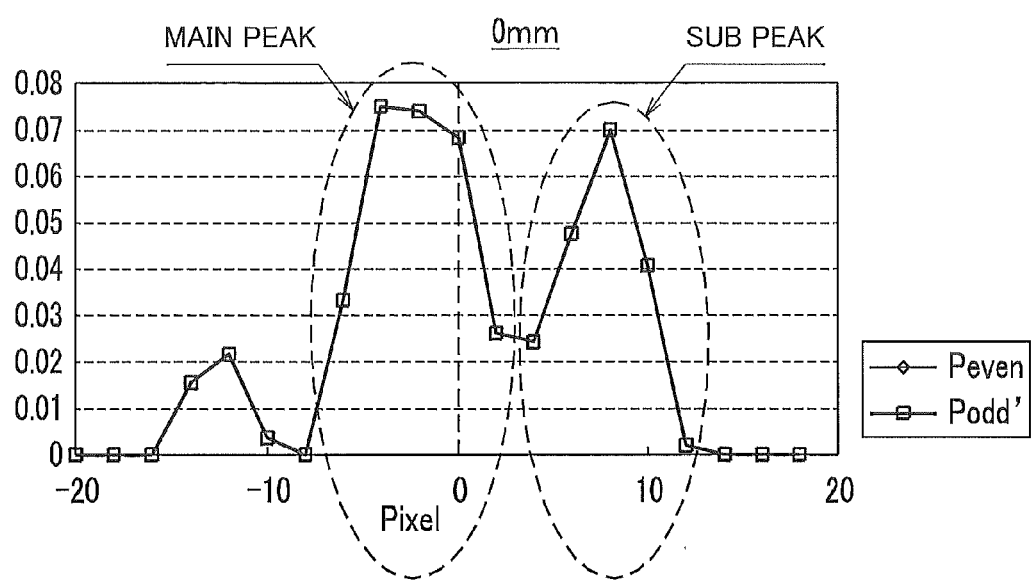
FIG. 19 is a diagram showing even numbered plots in the profiles $P_{even}$ and $P_{odd''}$.
Figures 20A, 20B, 20C, 20D:
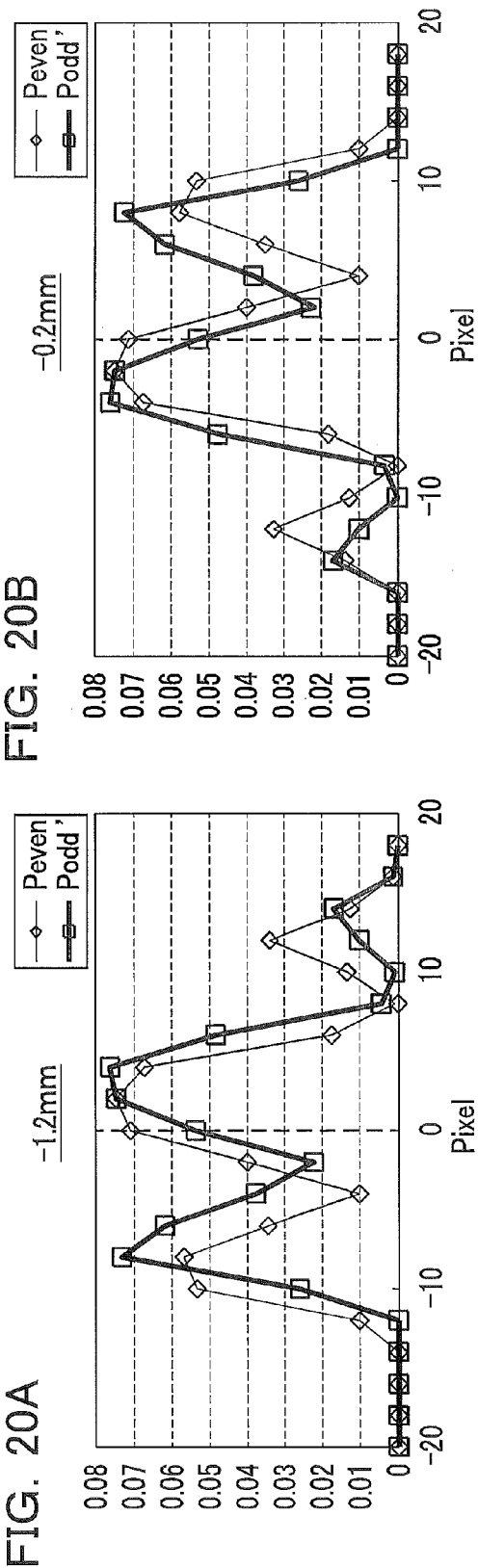
FIGS. 20A to 20D are diagrams showing the even-numbered plots in the profiles $P_{even}$ and $P_{odd'}$ and the collimator positional displacements, FIG. 20A showing the case where the positional displacement is −1.2 mm, FIG. 20B showing the case where the positional displacement is −0.2 mm, FIG. 20C showing the case where the positional displacement is 0.2 mm, and FIG. 20D showing the case where the positional displacement is 1.2 mm.

FIG. 19 shows a state where only the even-numbered pixels in $P_{even}$ and $P_{odd'}$ are plotted when there is no positional displacement of the collimator shown in FIG. 16 ($P_{even}$ and $P_{odd'}$ overlap with each other). FIG. 19 shows that the plotting of the even-numbered pixels brings about a main peak and a sub-peak. Such plotting also makes it easier to visually see if the collimator 26 is displaced in the positive direction or negative direction.

FIGS. 20A to 20D show $P_{even}$ and $P_{odd'}$ (only the even-numbered pixels are plotted) when the positional displacement of the collimator 26 is −1.2 mm, −0.2 mm, +0.2 mm and +1.2 mm. In the case where the collimator is displaced by +0.2 mm, for example, when the main peak of $P_{even}$ is located at the left of the main peak of $P_{odd'}$ and the sub-peak is located at the right of the main peak, the positional displacement is found from calculation to be occurring within a range of 0 mm to 0.7 mm in the positive direction.

Figure 21:
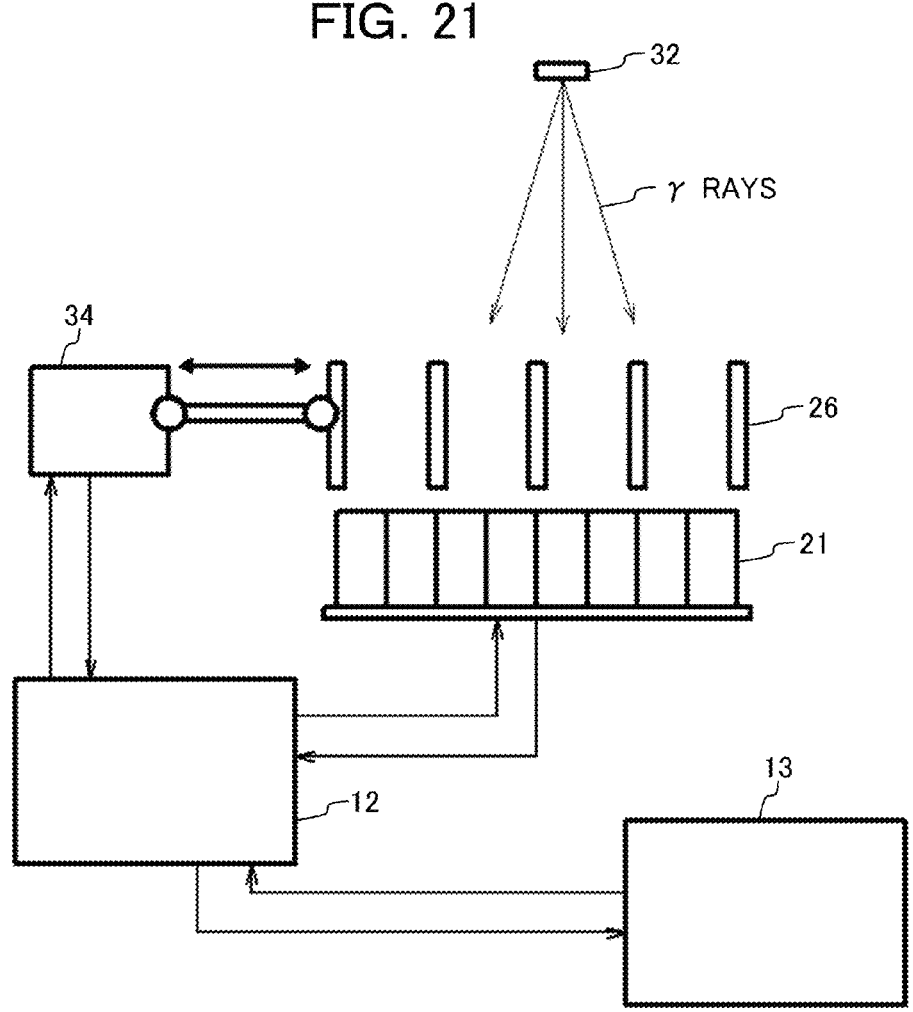
FIG. 21 is a block diagram showing alignment of the collimator by profile measurement of the radiation source.

Therefore, the positional displacement amount is estimated on FIG. 17 by obtaining the residual sum of squares of $P_{even}$ and $P_{odd'}$ through the measurement of the radiation source during alignment of the collimator 26. Then, the positional displacement direction is determined based on the positional relationship between the main peak and the sub-peak as shown in FIGS. 20A to 20D. Thereafter, a collimator moving mechanism 34 is used to move the collimator 26 for the positional displacement amount. This is capable of performing accurate alignment (see FIG. 21).

The collimator moving mechanism 34 may be configured to include, for example, an unillustrated motor and a connecting rod that is moved back and forth by the rotation of the motor to move the collimator 26. The collimator moving mechanism 34 is configured to operate upon receipt of a signal from the data processing device 12 as a positional displacement measuring unit, and to move the collimator 26 to a predetermined position. Note that more than one collimator moving mechanism 34 may be provided and operated to align the collimator 26.

Note that the positional displacement amount before or after the alignment of the collimator 26 may be displayed on the display device 13 (on a screen of a personal computer). Thus, an operator is informed of the positional displacement amount and a final result of the alignment. Note that, as for the display of the positional displacement, an alignment direction may also be displayed by an arrow or the like, thus enabling the operator to visually see a relative positional displacement.

Note that the collimator may also be manually aligned without using the collimator moving mechanism 34.

Note that the positional relationship between the main peak and the sub-peak is capable of being visually read from the profile. However, positions of the main peak and the sub-peak is capable of being obtained by a program for detecting peaks, and the positional displacement direction is capable of being automatically determined from the obtained positions of the main peak and the sub-peak.

Alternatively, a correlation between $P_{even}$ when there is a positional displacement (−1.4 to +1.4 mm) obtained by simulation and $P_{even}$ obtained beforehand by experiment is capable of being obtained (e.g., the residual sum of squares), and the positional displacement direction is capable of being determined from positional displacement information of $P_{even}$ obtained by simulation having the strongest correlation.

Figure 22:
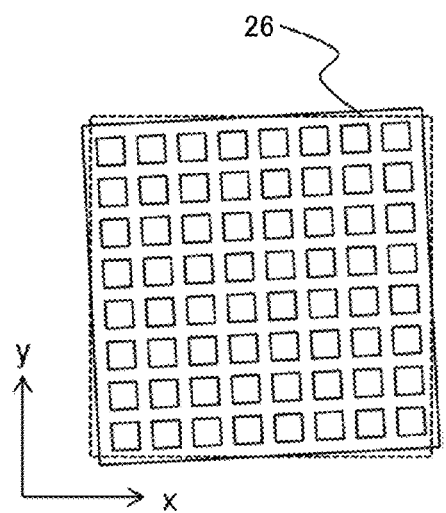
FIG. 22 is a diagram showing the collimator rotated within an xy plane.

Although the above description is given of the positional displacement in the x direction, positional displacement information for a positional displacement in the y direction is also capable of being obtained in the same manner. Furthermore, positional displacement information is also capable of being obtained in the same manner for the case where the collimator 26 is rotated as shown in FIG. 22. In this case, positional displacement information may be obtained from the profile of the radiation source in the x direction at both ends of the collimator 26 in the y direction, and positional displacement information may be similarly obtained from the profile of the radiation source in the y direction at both ends of the collimator 26 in the x direction.

Such determination of the positional displacement direction of the collimator 26 is performed by the data processing device 12.

Incidentally, the hole pitch (the pitch of the through-holes 27) may vary from one location of the collimator 26 to another according to manufacturing accuracy of the collimator 26. Alternatively, when a number of the detectors 21 are mounted for each module, an influence of a gap formed between the modules may change the detector pitch.

In such a case, it is difficult to eliminate the positional displacement between the collimator 26 and the detectors 21 in the entire region of the collimator 26. Therefore, positional displacements are measured at multiple locations (e.g., for each module), and the collimator 26 is aligned so as to minimize the sum of the positional displacement amounts in the respective modules. Alternatively, the collimator 26 is aligned such that the positional displacement amount is smaller than a positional displacement amount that causes no artifacts in a reconstructed image. In this event, by displaying the positional displacement amount at each location after the alignment of the collimator 26 on the display device 13 (on the screen of the personal computer), the operator may be informed of the final result of the alignment.

Furthermore, the positional displacement for each module may be displayed on the display device 13. Thus, the operator sees if the positional displacement occurs in the entire region or locally occurs in a certain module.

Alternatively, in each module, positional displacement amounts at multiple spots of the collimator in the x direction may be obtained, and the collimator 26 may be aligned in the x direction such that all the positional displacement amounts are smaller than a certain threshold. Likewise, positional displacement amounts at multiple spots of the collimator in the y direction may be obtained, and the collimator 26 may be aligned in the y direction such that all the positional displacement amounts are smaller than a certain threshold.

Although the above description is given of the case where four detectors (2×2) are included in each of the through-holes 27 in the collimator 26, the number of the detectors is not limited to four in this embodiment. The present invention is also applicable to the case where m detectors in the x direction and n detectors in the y direction (m×n detectors) are included in each of the through-holes 27 in the collimator 26. Here, m and n are integers.

Next, the alignment in the x direction is described. When the detector pixel positions are designated as a position counted from 0, it is assumed that a profile when the radiation source is disposed above the m×$i_x$-th ($i_x$ is an integer) detector pixel in the x direction is $P_a$, and a profile when the radiation source is disposed above the m×$i_x$+(m−1)th detector pixel is $P_b$. Here, m×$i_x$ and m×$i_x$+(m−1) as the positions of the detector pixels correspond respectively to the positions of the detector pixel in the positive direction and the detector pixel in the negative direction, which are closest to the ceptor 28 of the collimator 26. In this event, $P_b$ is inverted about the detector pixel position m×$i_x$+(m−1)/2 to obtain $P_b'$.

Then, the residual sum of squares of $P_a$ and $P_b'$ obtained by actual measurement is obtained, and a positional displacement amount Dx in the x direction is estimated from a graph of a relationship between the amount of positional displacement of the collimator 26 and the residual sum of squares of $P_a$ and $P_b'$.

Next, only the m×$j_x$-th ($j_x$ is an integer) values in $P_a$ and $P_b'$ are plotted to obtain $p_a$ and $p_b'$, and a positional displacement direction is determined based on a positional relationship between main peaks and sub-peaks of $p_a$ and $p_b'$.

Likewise, it is possible to obtain a positional displacement amount in the y direction and a positional displacement direction in the y direction.

In the alignment in the y direction, when the detector pixel positions are designated as numbers counted from 0, it is assumed that a profile measured when the radiation source is disposed above the n×$i_y$-th ($i_y$ is an integer) detector pixel in the y direction is $P_c$, and a profile measured when the radiation source is disposed above the n×$i_y$+(n−1)th detector pixel is $P_d$. In this event, $P_d$ is inverted about the detector pixel position $n \times i_y + (n-1)/2$ to obtain $P_d'$.

Then, the residual sum of squares of $P_c$ and $P_d'$ obtained by actual measurement is obtained, and a positional displacement amount Dy in the y direction is estimated from a graph of a relationship between the amount of positional displacement of the collimator 26 and the residual sum of squares of $P_c$ and $P_d'$.

The radiation image acquiring device according to this embodiment described above optimally corrects a positional displacement between the detector 21 (the group of detectors 21A) and the collimator 26 based on positional displacement information obtained by measuring the positional displacement between the detector 21 (the group of detectors 21A) and the collimator 26 by using a radiation source profile measured by the detector 21 based on the radiation source disposed corresponding to a predetermined detector 21. Therefore, the radiation image acquiring device capable of acquiring an image without artifacts is achieved.

Moreover, during the alignment of the collimator 26, by obtaining the residual sum of squares of $P_{even}$ and $P_{odd}$ through the measurement based on an arbitrary radiation source, a positional displacement amount is capable of being estimated from the graph (FIG. 17) showing a relationship between the amount of positional displacement of the collimator 26 in the x direction and the residual sum of squares of $P_{even}$ and $P_{odd}'$. Thus, the positional displacement between the detector 21 (the group of detectors 21A) and the collimator 26 is optimally corrected. Therefore, the radiation image acquiring device capable of acquiring an image without artifacts is achieved.

Second Embodiment

A radiation image acquiring device according to this embodiment performs alignment of a collimator 26 by measuring a profile of a radiation source disposed immediately above an intermediate position between detector pixels, immediately above the position of a ceptor 28 of the collimator 26, or immediately above an intermediate position between the ceptors 28.

As shown in FIG. 14, in a configuration in which four detectors 21 are included in each of through-holes 27 in the collimator 26, a profile obtained when the radiation source is disposed above the even-numbered detector pixel has a distribution that is asymmetric about the position where the radiation source is disposed.

Figure 23:
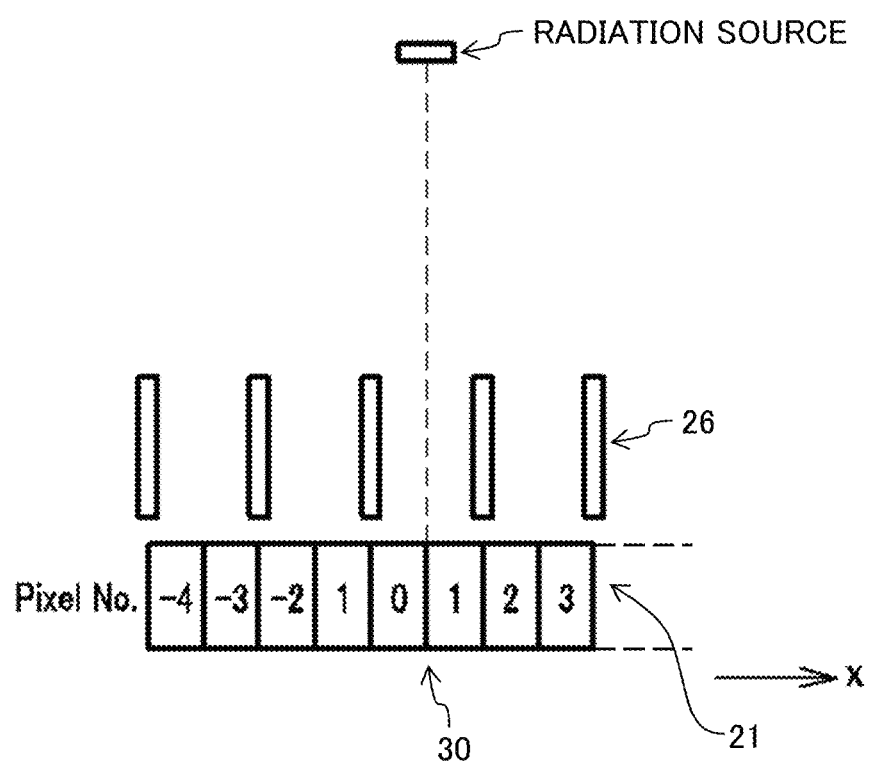
FIG. 23 is a diagram showing a positional relationship among the radiation source, the collimator and the detector during measurement of a positional displacement of the collimator.

Meanwhile, when there is no displacement of the collimator 26, as shown in FIG. 23, a profile obtained when the radiation source is disposed immediately above an intermediate position between the even-numbered and odd-numbered detector pixels has a distribution that is symmetric about the position where the radiation source is disposed. Using this, the alignment of the collimator 26 is capable of being performed by measuring a profile while disposing the radiation source immediately above the intermediate position between the detector pixels (a boundary surface 30 between the detectors 21), obtaining an asymmetry degree of the profile, and moving the collimator 26 so as to minimize the asymmetry degree.

For example, as shown in FIG. 18, the line source 33 is disposed, a profile in the x direction is obtained for each of the detector pixel positions in the y direction, and the position of the centroid of each profile in the x direction is obtained. Then, an average value of the profiles is obtained, in which the position of the centroid in the x direction is at the intermediate position between the detector pixels, and the collimator 26 is moved so as to minimize the asymmetry degree of the averaged profile.

This method is not limited to the case where four detectors 21 are included in each of the through-holes 27 in the collimator 26. With the method generalized into a configuration in which a number of detectors 21 are included in each of the through-holes 27 in the collimator 26, the alignment of the collimator is capable of being performed by measuring a profile of a radiation source disposed immediately above the position of the ceptor 28 of the collimator 26 or immediately above the intermediate position between the ceptors 28, obtaining an asymmetry degree of the profile, and moving the collimator 26 so as to minimize the asymmetry degree.

Although the present invention has been described above, the present invention is not limited to the above embodiments, but is capable of being implemented by making appropriate changes.

While the point radiation source, the line source or the like is used as the radiation source in the above embodiments, the present invention is not limited thereto. A point radiation source obtained by collimating an X-ray source may be used as the radiation source. Thus, the X-ray source may be optimally used as the point radiation source. Alternatively, a line source obtained by collimating an X-ray source may be used as the radiation source. Thus, the X-ray source is optimally used as the line source.

REFERENCE SIGNS LIST 12 data processing device (positional displacement measuring unit)
13 display device
21 detector
21A group of detectors
26 collimator
27 through-hole
28 ceptor

The invention claimed is:

1. A radiation image acquiring device comprising:
a plurality of detectors to measure radiation;
a collimator including a plurality of through-holes having the detectors disposed therein and configured to limit an incident direction of the radiation; and
a data processing device to measure a positional displacement between the detectors and the collimator by use of profiles of a radiation source measured by the detectors,
wherein:
pixels of the detectors are two-dimensionally arranged in an x direction and a y direction, where m detectors in the x direction and n detectors in the y direction (m×n detectors), where m and n are integers, are included in single ones of the through-holes of the collimator,
$P_a$ denotes one of the profiles in the x direction measured when the radiation source is disposed above the $m \times i_x$-th ($i_x$ is an integer) detector pixel position in the x direction, which is designated as a position counted from 0,
$P_b$ denotes one of the profiles in the x direction measured when the radiation source is disposed above the $m \times i_x + (m-1)$th detector pixel, and
$P_b$ is inverted about the detector pixel position $m \times i_x + (m-1)/2$ to obtain $P_b'$, wherein the data processing device sets an amount of movement of the collimator in the x direction such that a residual sum of squares $R_x$ of $P_a$ and $P_b'$ is less than a predetermined threshold, wherein:

$P_c$ denotes one of the profiles measured when the radiation source is disposed above the $n \times i_y$-th ($i_y$ is an integer) detector pixel position in the y direction, which is designated as a position counted from 0, $P_d$ denotes one of the profiles measured when the radiation source is disposed above the $n \times i_y + (n-1)$th detector pixel, and $P_d$ is inverted about the detector pixel position $n \times i_y + (n-1)/2$ to obtain $P_d'$, and wherein the data processing device sets an amount of movement of the collimator in the y direction such that a residual sum of squares $R_y$ of $P_c$ and $P_d'$ is less than the predetermined threshold.

2. The radiation image acquiring device according to claim 1, wherein the data processing device sets an amount of movement of the collimator in the x direction so as to minimize $R_x$, and wherein the data processing device sets an amount of movement of the collimator in the y direction so as to minimize $R_y$.

3. The radiation image acquiring device according to claim 1, wherein the data processing device estimates a positional displacement amount $D_x$ in the x direction from $R_x$, an amount of positional displacement of the collimator obtained beforehand, and a graph showing a relationship of the residual sum of squares of $P_a$ and $P_b'$, wherein the data processing device sets $D_x$ as an amount of movement of the collimator in the x direction so as to minimize $R_x$, wherein the data processing device estimates a positional displacement amount $D_y$ in the y direction from $R_y$, an amount of positional displacement of the collimator obtained beforehand, and a graph showing a relationship of the residual sum of squares of $P_c$ and $P_d'$, and wherein the data processing device sets $D_y$ as an amount of movement of the collimator in the y direction so as to minimize $R_y$.

4. The radiation image acquiring device according to claim 1, wherein the data processing device obtains $p_a$ and $p^{b'}$ by plotting only the $m \times j_x$-th ($j_x$ is an integer) values in $P_a$ and $P_b'$, wherein the data processing device determines a direction of positional displacement in the x direction based on a positional relationship between main peaks and sub-peaks of $p_a$ and $p_b'$, wherein the data processing device obtains $p_c$ and $p_d'$ by plotting only the $n \times j_y$-th ($j_y$ is an integer) values in $P_c$ and $P_d'$, and wherein the data processing device determines a direction of positional displacement in the y direction based on a positional relationship between main peaks and sub-peaks of $p_c$ and $p_d'$.

5. The radiation image acquiring device according to claim 1, wherein the data processing device obtains beforehand $P_a$ as $P_a(x)$ which is a positional displacement x obtained by simulation in a range of $-H_x/2$ to $H_x/2$, where $H_x$ denotes a hole pitch of the collimator in the x direction, wherein the data processing device obtains a residual sum of squares of $P_a(x)$ obtained by simulation and $P_a$ obtained during positional displacement measurement, wherein the data processing device obtains a direction of positional displacement in the x direction from the value of the positional displacement x of $P_a(x)$ where the residual sum of squares of $P_a(x)$ and $P_a$ is minimized, wherein the data processing device obtains beforehand $P_c$ as $P_c(y)$ which is a positional displacement x obtained by simulation in a range of $-H_y/2$ to $H_y/2$, where $H_y$ denotes a hole pitch of the collimator in the y direction, wherein the data processing device obtains a residual sum of squares of $P_c(y)$ obtained by simulation and $P_a$ obtained during positional displacement measurement, and wherein the data processing device obtains a direction of positional displacement in the y direction from the value of the positional displacement y of $P_c(y)$ where the residual sum of squares of $P_c(y)$ and $P_c$ is minimized.

6. The radiation image acquiring device according to claim 1, wherein the data processing device obtains positional displacement information from profiles of the radiation source in the x direction at both ends of the collimator in the y direction, wherein the data processing device sets different movement amounts at both the ends of the collimator in the y direction so as to move the collimator in the x direction, wherein the data processing device obtains positional displacement information from profiles of the radiation source in the y direction at both ends of the collimator in the x direction, and wherein the data processing device sets different movement amounts at both the ends of the collimator in the x direction so as to move the collimator in the y direction.

7. The radiation image acquiring device according to claim 1, wherein the data processing device obtains positional displacement amounts at spots of the collimator in the x direction, and sets an amount of movement of the collimator in the x direction so as to minimize the sum of the positional displacement amounts at the spots of the collimator in the x direction, wherein the data processing device obtains positional displacement amounts at spots of the collimator in the y direction, and wherein the data processing device sets an amount of movement of the collimator in the y direction so as to minimize the sum of the positional displacement amounts at the spots of the collimator in the y direction.

8. The radiation image acquiring device according to claim 1, wherein the data processing device obtains positional displacement amounts at spots of the collimator in the x direction, wherein the data processing device sets an amount of movement of the collimator in the x direction such that the positional displacement amounts at the spots of the collimator in the x direction are smaller than a predetermined threshold, wherein the data processing device obtains positional displacement amounts at spots of the collimator in the y direction, and wherein the data processing device sets an amount of movement of the collimator in the y direction such that the positional displacement amounts at the spots of the collimator in the y direction are smaller than a predetermined threshold.

9. The radiation image acquiring device according to claim 1, wherein
the data processing device data processing device identifies the position of the radiation source relative to the detectors.

10. The radiation image acquiring device according to claim 9,
wherein the data processing device obtains the position of the radiation source from a position of a centroid of the profiles,
wherein the position identification unit obtains the position of the centroid of the profile of the radiation source expressed by the count in the vertical axis and the position of the detector in the horizontal axis while designating the position of the detector with an integer counted from 0, and
wherein the position identification unit sets a value obtained by rounding the position of the centroid as the position of the radiation source.

11. The radiation image acquiring device according to claim 1,
wherein the radiation source is a line source,
wherein the line source is disposed at an angle with respect to the y direction when the profiles in the x direction are obtained,
wherein the line source is disposed at an angle with respect to the x direction when profiles in the y direction are obtained, and
wherein the data processing device obtains positional information of the collimator by using $P_a$ and $P_b$, obtained by:
when obtaining the profiles in the x direction, obtaining the profiles in the x direction for each detector pixel position in the y direction, designating the position of the detector with an integer counted from 0, obtains the position of the centroid of the profile of the radiation source expressed by the position of the detector in the horizontal axis and the count in the vertical axis, setting a value obtained by rounding the position of the centroid as a radiation source position in the x direction, and setting average values of the profiles in which the radiation source positions are $m \times i_x$-th and $m \times i_x+(m-1)$th positions as $P_a$ and $P_b$, and
wherein the data processing device obtains positional information of the collimator by using $P_c$ and the $P_d$, obtained by:
when obtaining the profiles in the y direction, obtaining the profiles in the y direction for each detector pixel position in the x direction, designating the position of the detector with an integer counted from 0, obtains the position of the centroid of the profile of the radiation source expressed by the position of the detector in the horizontal axis and the count in the vertical axis, setting a value obtained by rounding the position of the centroid as a radiation source position in the y direction, and setting average values of the profiles in which the radiation source positions are $n \times i_y$-th and $n \times i_y+(n-1)$th positions as $P_c$ and $P_d$.

12. The radiation image acquiring device according to claim 1,
wherein collimator has a plurality of ceptors which define the through-holes,
wherein the data processing device measures the profiles of the radiation source disposed immediately above the position of one of the ceptors of the collimator or immediately above an intermediate position between the ceptors, and
wherein the data processing device obtains an asymmetry degree of the profiles, and
wherein the data processing device sets an amount of movement of the collimator so as to minimize the asymmetry degree.

13. An alignment method for a radiation image acquiring device comprising:
arranging a plurality of detectors to measure radiation and a collimator including a plurality of through-holes having the detectors disposed therein and configured to limit an incident direction of the radiation, so that pixels of the detectors are two-dimensionally arranged in an x direction and a y direction, where m detectors in the x direction and n detectors in the y direction (m×n detectors), where m and n are integers, are included in single ones of the through-holes of the collimator;
setting an amount of movement of the collimator in the x direction such that a residual sum of squares $R_x$ of Pa and Pb' is less than a predetermined threshold, where:
$P_a$ denotes one of the profiles in the x direction measured when the radiation source is disposed above the $m \times i_x$-th ($i_x$ is an integer) detector pixel position in the x direction, which is designated as a position counted from 0,
$P_b$ denotes one of the profiles in the x direction measured when the radiation source is disposed above the $m \times i_x+(m-1)$th detector pixel, and
$P_b$ is inverted about the detector pixel position $m \times i_x+(m-1)/2$ to obtain $P_b'$;
moving the collimator by the set amount of movement in the x direction;
setting an amount of movement of the collimator in the y direction such that a residual sum of squares $R_y$ of $P_c$ and $P_d'$ is less than the predetermined threshold, where:
$P_c$ denotes one of the profiles measured when the radiation source is disposed above the $n \times i_y$-th ($i_y$ is an integer) detector pixel position in the y direction, which is designated as a position counted from 0,
$P_d$ denotes one of the profiles measured when the radiation source is disposed above the $n \times i_y+(n-1)$th detector pixel, and
$P_d$ is inverted about the detector pixel position $n \times i_y+(n-1)/2$ to obtain $P_d'$; and
moving the collimator by the set amount of movement in the y direction.

14. The alignment method according to claim 13, wherein the amount of movement of the collimator in the x direction is set to minimize $R_x$, and
wherein the amount of movement of the collimator in the y direction is set to minimize $R_y$.

15. The alignment method according to claim 13, further comprising:
estimating a positional displacement amount $D_x$ in the x direction from $R_x$, an amount of positional displacement of the collimator obtained beforehand, and a graph showing a relationship of the residual sum of squares of $P_a$ and $P_b'$;
setting $D_x$ as an amount of movement of the collimator in the x direction so as to minimize $R_x$;
estimating a positional displacement amount $D_y$ in the y direction from $R_y$, an amount of positional displacement of the collimator obtained beforehand, and a graph showing a relationship of the residual sum of squares of $P_c$ and $P_d'$; and setting $D_y$ as an amount of movement of the collimator in the y direction so as to minimize $R_y$.

16. The alignment method according to claim 13, further comprising:
providing $P_a$ as $P_a(x)$ which is a positional displacement x obtained by simulation in a range of $-H_x/2$ to $H_x/2$, where $H_x$ denotes a hole pitch of the collimator in the x direction;
obtaining a residual sum of squares of $P_a(x)$ obtained by simulation and $P_a$ obtained during positional displacement measurement;
obtaining a direction of positional displacement in the x direction from the value of the positional displacement x of $P_a(x)$ where the residual sum of squares of $P_a(x)$ and $P_a$ is minimized;
providing $P_c$ as $P_c(y)$ which is a positional displacement x obtained by simulation in a range of $-H_y/2$ to $H_y/2$, where $H_y$ denotes a hole pitch of the collimator in the y direction;
obtaining a residual sum of squares of $P_c(y)$ obtained by simulation and $P_a$ obtained during positional displacement measurement; and
obtaining a direction of positional displacement in the y direction from the value of the positional displacement y of $P_c(y)$ where the residual sum of squares of $P_c(y)$ and $P_c$ is minimized.

17. The alignment method according to claim 13,
wherein the positional displacement information from profiles of the radiation source in the x direction is obtained at both ends of the collimator in the y direction,
wherein different movement amounts are set at both the ends of the collimator in the y direction so as to move the collimator in the x direction,
wherein the positional displacement information from profiles of the radiation source in the y direction is obtained at both ends of the collimator in the x direction, and
wherein different movement amounts are set at both the ends of the collimator in the x direction so as to move the collimator in the y direction.

18. The alignment method according to claim 13,
wherein the radiation source is a line source,
wherein the line source is disposed at an angle with respect to the y direction when the profiles in the x direction are obtained, and
wherein the line source is disposed at an angle with respect to the x direction when profiles in the y direction are obtained.

* * * * *